United States Patent [19]

Möller et al.

[11] Patent Number: 4,562,068

[45] Date of Patent: Dec. 31, 1985

[54] SEBOSUPPRESSIVE COSMETIC PREPARATIONS CONTAINING ARYLOXOBUTENOIC ACID DERIVATIVES

[75] Inventors: Hinrich Möller; Siegfried Wallat, both of Monhein, Fed. Rep. of Germany

[73] Assignee: Henkel Kommanditgesellschaft auf Aktien, Dusseldorf-Holthausen, Fed. Rep. of Germany

[21] Appl. No.: 458,963

[22] Filed: Jan. 18, 1983

[30] Foreign Application Priority Data

Aug. 2, 1982 [DE] Fed. Rep. of Germany ....... 3228842

[51] Int. Cl.⁴ ............................................... A61K 7/06
[52] U.S. Cl. .................................... 424/70; 514/545;
546/314; 549/13; 549/505; 560/51; 560/53;
560/19; 562/459; 564/169

[58] Field of Search ...................... 560/51, 53; 424/70;
514/545

[56] References Cited

FOREIGN PATENT DOCUMENTS 2480600 10/1981 France ................................... 560/51
2075836 11/1981 United Kingdom .................. 560/51

OTHER PUBLICATIONS

Christidis, Y. et al., CA 96(16):129796a, Fr. Demande FR 2481118 A1, Oct. 30, 1981.

*Primary Examiner*—Paul J. Killos
*Attorney, Agent, or Firm*—Hammond & Littell, Weissenberger & Dippert

[57] ABSTRACT

This invention relates to a topical cosmetic preparation for treating oily hair or seborrhea which contains a sebosuppressively effective amount of at least one 4-aryl-4-oxo-but-2-enoic acid derivative.

7 Claims, No Drawings

SEBOSUPPRESSIVE COSMETIC PREPARATIONS CONTAINING ARYLOXOBUTENOIC ACID DERIVATIVES

FIELD OF THE INVENTION

This invention relates to topical cosmetic preparations. More particularly, this invention relates to topical cosmetic preparations which contain aryloxobutenoic acid derivatives and which are useful in treating oily hair and seborrehic skin.

BACKGROUND OF THE INVENTION

Excessive excretion of the sebaceous glands in the scalp gives hair an oily appearance that generally is considered esthetically unappealing. Consequently, there have been many attempts to make such glands secrete normally by suitable means, to restore a healthy look to the hair. Cosmetic preparations containing sulfur, mercury, or tar have been used to fight seborrhea on the head. It has been found that prolonged use of these known anti-seborrehic additives frequently produces side effects without yielding really satisfactory results as far as their effectiveness and application properties are concerned. German published patent application (DE-OS) No. 29 26 267 mentions 3,7,11-trimethyl-2,6,10-dodecatrien-1-ol derivatives as an additive to cosmetic preparations to normalize sebum secretion. However, it has been found that these compounds have a very low antiseborrheic effect.

OBJECTS OF THE INVENTION

It is an object of the invention to provide topical cosmetic preparations.

It is also an object of the invention to provide topical cosmetic preparations useful in treating oily hair and seborrhea.

It is a further object of the invention to provide topical cosmetic preparations containing aryloxobutenoic acid derivatives.

These and other objects of the invention will become more apparent in the discussion below.

DETAILED DESCRIPTION OF THE INVENTION

Applicants have now discovered topical cosmetic preparations which are especially effective in the treatment of seborrhea and strongly oily hair. These topical cosmetic preparations contain aryloxobutenoic acid derivatives, even in very small amounts. More particularly, the sebosuppressive cosmetic preparations contain 4-aryl-4-oxo-but-2-enoic acid derivatives of the formula

Ar—CO—CH=CH—CO—X    (I)

wherein
   Ar represents an optionally substituted hydrocarbon aromatic or heteroaromatic group; and
   X represents an alkoxy group having from 1 to 10 carbon atoms, an amine group optionally substituted by one or more aryl or alkyl groups having from 1 to 6 carbon atoms, or a nitrogen atom-containing heterocycle.

More particularly, the sebosuppressive cosmetic preparations contain a sebosuppressively effective amount of at least one compound of Formula I wherein:

Ar is a member selected from the group consisting of (1) hydrocarbon aryl, (2) hydrocarbon aryl substituted with substituents selected from the group consisting of halogen, alkyl having from 1 to 6 carbon atoms, alkoxy having from 1 to 8 carbon atoms, hydroxyl, amino, alkylamino having from 1 to 4 carbon atoms, dialkylamino having from 2 to 8 carbon atoms, and alkanoylamino having from 1 to 4 carbon atoms, dialkylamino having from 2 to 8 carbon atoms, and alkanoylamino having from 1 to 4 carbon atoms, (3) monocyclic heteroaryl containing heteroatoms selected from the group consisting of nitrogen, sulfur, and oxygen, (4) benzo analogs of said monocyclic heteroaryl, and (5) substituted monocyclic heteroaryl containing heteroatoms selected from the group consisting of nitrogen, sulfur, and oxygen, substituted with alkyl having from 1 to 6 carbon atoms, and X is a member selected from the group consisting of (6) alkoxy having from 1 to 10 carbon atoms, (7) phenylalkoxy having from 7 to 10 carbon atoms, (8) phenacyloxy, (9) amino having the formula

wherein $R_1$ is a member selected from the group consisting of alkyl having from 1 to 6 carbon atoms, hydroxyalkyl having from 1 to 6 carbon atoms, alkoxyalkyl having from 2 to 6 carbon atoms, and phenylalkyl where the alkyl moiety has from 1 to 6 carbon atoms and $R_2$ is a member selected from the group consisting of hydrogen and $R_1$, and $R_1$ and $R_2$ taken together are members selected from the group consisting of alkylene having 4 or 5 carbon atoms, akylalkylene having from 5 to 10 carbon atoms, oxaalkylene having 4 or 5 carbon atoms, and alkyloxaalkylene having from 5 to 10 carbon atoms.

Examples of Ar include phenyl, α- or β-naphthyl, pyridyl, thienyl, furyl, and a corresponding benzo analogue, any of which may be substituted or unsubstituted. Suitable substituents include one or more halogen atoms, preferably chlorine, alkyl groups having from 1 to 6 carbon atoms, alkoxy groups having from 1 to 8 carbon atoms, hydroxyl groups, amino groups, alkylamino and dialkylamino groups having from 1 to 6 carbon atoms in each alkyl, and acylamino groups having from 1 to 4 carbon atoms. More particularly, the 4-Ar could be any one of the following: phenyl, 1'-naphthyl, 2'-naphthyl, 4'-methyl-phenyl, 2',4'-dimethyl-phenyl, 2',5'-dimethyl-phenyl, 3',4'-dimethyl-phenyl, 2',4',6'-trimethyl-phenyl, 2',4',5'-trimethyl-phenyl, 4'-chloro-phenyl, 2',4'-dichloro-phenyl, 2',5'-dichlorophenyl, 2',4',6'-trichlorophenyl, 4'-methoxy-phenyl, 4'-butoxy-phenyl, 4'-hexyloxy-phenyl, 4'-octyloxy-phenyl, 2',4'-dimethoxy-phenyl, 2',5'-dimethoxy-phenyl, 3',4'-dimethoxy-phenyl, 2',3',4'-trimethoxy-phenyl, 2',4',6'-trimethoxy-phenyl, 4'-tert.butyl-phenyl, 3',4'-dimethoxy-2'-hydroxy-phenyl, 3'-tert.butyl-2'-hydroxyphenyl, 3',5'-di-tert.butyl-4'-hydroxy-phenyl, 4'-aminophenyl, 2',4'-diamino-phenyl, 4'-acetylamino-phenyl, 4'-hydroxy-phenyl, 4'-dimethylamino-phenyl, 2',6'-dichloro-4'-methoxy-phenyl, 2',3'-dichloro-4'-methoxyphenyl, 2',4'-dichloro-5'-methyl-phenyl, 2',5'-dichloro- 3',6'-dimethyl-phenyl, 2'-chloro-4'-methoxy-phenyl, 2'-chloro-4'-methyl-phenyl, 2'-chloro-4',6'-dimethoxy-phenyl, 2'-chloro-4',5'-dimethyl-phenyl, 2'-thienyl, 3',4'-dimethyl-3'-thienyl, 2'-furyl, or 3'-pyridyl.

When the compounds of Formula I are ester derivatives, that is, X represents an alkoxy group, X can be, for example, a methoxy, ethoxy, propoxy, isopropoxyl, n-butoxy, isobutoxy, sec.butoxy, tert.butoxy, pentoxy, hexoxy, octoxy, 2-ethylhexoxy, decoxy, benzoxy, or phenacyloxy group. If the compounds of Formula I are amides, that is, if X represents a substituted amino group or a nitrogen atom-containing heterocycle, then X may be selected from the following group: methylamino, dimethylamino, ethylamino, diethylamino, propylamino, dipropylamino, methylpropylamino, 2-propylamino, di-2-propylamino, butylamino, dibutylamino, 2-butylamino, sec.butylamino, tert.butylamino, hexylamino, dihexylamino, 2-ethylhexylamino, octylamino, ethyloctylamino, decylamino, dodecylamino, 2-hydroxyethylamino, di-(2-hydroxy-isopropyl)-amino, 3-methoxy-propyl-amino, 3-(2-ethyl-hexoxy)-propylamino, benzylamino, anilino, N-methyl-anilino, piperidino, 2-methyl-piperidino, 3-methyl-piperidino, 4-methyl-piperidino, 2,6-dimethyl-piperidino, 3,5-dimethyl-piperidino, morpholino, and 2,6-dimethyl-morpholino.

The compounds of the invention can be prepared by generally known methods. Preferably acids of the formula

Ar—CO—CH=CH—COOH     (II)

wherein Ar is as devined above, are used as starting materials, which acids can then be transformed into ester or amide derivatives by conventional procedures. The acids of Formula II can be prepared by Friedel-Crafts reaction of optionally substituted aromatics with maleic acid anhydride in the presence of a Friedel-Crafts catalyst. Moreover, the esters and amides are also accessible directly by Friedel-Crafts reaction with β-chlorocarbonyl-acrylic acid esters or amides. Another possibility of ester synthesis is the condensation of glyoxylic acid esters with suitably substituted acetyl aromatics or heteroaromatics.

The compounds of Formula I are well tolerated by the skin and mucous membranes and can be easily incorporated into various cosmetic preparations, such as aqueous, alcoholic, or aqueous alcoholic solutions, oils, suspensions, gels, emulsions, ointments, pastes, or aerosols. For the treatment of seborrhea and oily hair, the active ingredients of Formula I can be used in all conventional application forms, such as, hair lotions, hair shampoos, hair conditioners, hair rinses, skin lotions, or shaking mixtures. Use in hair cosmetics is preferred. In addition to the active substances according to the invention, these cosmetic preparations can contain known vehicles and additives such as water, organic solvents, surface-active compounds, oils, fats, waxes, perfume, dyes, preservatives, and the like.

The sebosuppressive topical cosmetic preparations of the invention contain at least one aryloxobutenoic acid derivative in an amount sufficient to impart anti-seborrheic properties. The cosmetic preparations preferably contain from about 0.01 to 5.0 percent by weight, more preferably from about 0.05 to 1.0 percent by weight, based upon the total weight of the cosmetic preparation, of the aryloxobutenoic acid derivatives.

The following examples are intended to illustrate the invention and should not be construed as limiting it thereto.

EXAMPLES

PREPARATION OF COMPOUNDS OF FORMULA I

Example 1

4-(4'-Chloro-phenyl)-4-oxo-but-2-enoic acid ethyl ester

Fifteen grams (92 m mol) of fumaric acid monomethyl ester chloride were added dropwise under stirring over a period of 25 minutes to a mixture of 200 ml of chlorobenzene and 18.4 gm (138 m mol) of aluminum chloride at 20° C. After heating for 45 minutes at 40° C., the mixture was cooled, poured on ice/water containing 30 ml of concentrated hydrochloric acid, and taken up in methylene chloride, and the solution was evaporated (under reduced pressure toward the end). The residue was recrystallized from petroleum ether, and 5.7 gm of pure 4-(4'-chlorophenyl)-4-oxo-but-2-enoic acid ethyl ester (melting point: 58°–60° C.) were obtained.

By use of procedures analogous to that described above, the compounds listed below were prepared, purification being carried out in the case of liquid substances partly by column chromatography (Si-O$_2$/CH$_2$Cl/methyl alcohol). In the preparation of other substituted phenyl derivatives, 1,2-dichloroethane was used as solvent.

Example 2

4-Phenyl-4-oxo-but-2-enoic ethyl ester

Boiling point: 117°–119° C./0.5 mbar; $n_D^{20} = 1.5423$.

Example 3

4-Phenyl-4-oxo-but-2-enoic isopropyl ester

Boiling point: 120°–122° C./0.6 mbar; $n_D^{20} = 1.5321$.

Example 4

4-Phenyl-4-oxo-but-2-enoic acid butyl ester

Boiling point: 140° C./0.9 mbar; $n_D^{20} = 1.5282$.

Example 5

4-(3',4'-Dimethoxy-phenyl)-4-oxo-but-2-enoic acid ethyl ester

Boiling point: 87°–89° C.

Example 6

4-(4'-Butoxy-phenyl)-4-oxo-but-2-enoic acid ethyl ester $n_D^{20} = 1.5494$.

Example 7

4-(4'-Octyloxy-phenyl)-4-oxy-but-2-enoic acid ethyl ester

Melting point: 46°–48° C.

Example 8

4-(3',4'-Dimethoxy-2'-hydroxy-phenyl)-4-oxo-but-2-enoic acid ethyl ester

Prepared from 1,2,3-trimethoxy-benzene.
Melting point: 102°–105° C.

Example 9

4-(4'-Acetylamino-phenyl)-4-oxo-but-2-enoic acid ethyl ester

Melting point: 126°–129° C.

Example 10

4-(2',4'-Dichloro-phenyl)-4-oxo-but-2-enoic acid ethyl ester

Melting point: 58°–61° C.

Example 11

4-Phenyl-4-oxo-but-2-enoic acid diethylamide $n_D^{20} = 1.56666$.

Testing for Anti-seborrheic Activity

The anti-seborrheic activity of aryloxobutenoic acid derivatives was examined closely in the animal experiments described hereinafter. The experimental animals were male Wistar rats weighing from 220 to 230 gm. A degree of brown discoloration on the shaved backs of the rats was established visually; the brown discoloration was caused by the brown cutaneous surface lipid of the rats. This test is based upon the observation that young female rats as well as male rats that were washed with tenside solution and a lipid solvent, respectively, as well as male rats that were treated systematically with estrogen, show only the normal light-colored pink skin after shaving; parallel to this, only relatively very small amounts of lipid can be extracted from the shorn hair.

For evaluation of anti-seborrheic activity, the test substances set forth in the table below, each in solution in ethanol, were each brushed on one side of the back fur of six rats. The other side was treated only with the solvent without the active substance (control side). During the testing period of 14 days, application of test substance was made once a day on a total of 9 days. A group of 6 rats that remained completely untreated served as an additional control. At the end of the testing, the animals were shaved on the back and the flanks and inspected visually, this inspection being done independently by an evaluation panel (6 persons) under doubleblind conditions.

Evaluation methods

Three criteria were rated. The first criterion was whether the majority of the evaluators recognized the treated side properly. The differentiations were as follows:

| Symbol | Percentage of evaluators recognizing an effect |
|---|---|
| ++ | 100% |
| + | >50% to <100% |
| − | ≦50% |

The second criterion was the difference between the right and left sides, one point each to be given per evaluator and animal, in the manner that the darker side was rated 1, the lighter side was rated 0, and uniformity of both sides were rated 0.5.

Significant differences between the untreated and the treated side according to the second method of evaluation indicate the topical effectiveness of a substance.

The third criterion was the rating of the difference in intensity of the brown shades according to the following scale:

| | |
|---|---|
| dark brown | 3 points |
| medium brown | 2 points |
| light brown | 1 point |
| no brown coloration | 0 points |

According to the third method of evaluation, the differences in the point totals between the untreated control animals and the treated and untreated sides, respectively, of the experimental animal group were calculated where significant differences between control animals and the treated side of the experimental animals indicate the effect of a substance. Similarly, a distinct difference between the untreated and the treated sides of the experimental animal groups is also generally noticeable. However, this is not always as distinct as that between control animals and treated sides, which may be due to various reasons, as, for example, mechanical transfer of substance from one side to the other or solvent influence.

The differentiation of the effects according to the methods of evaluation 2 and 3 was characterized in the following manner:

| Symbol | Difference in points |
|---|---|
| ++ | very great (>99.9 probability) |
| + | significant (≧95% probability) |
| − | (<95% probability) |

The results of the evulations of the test substances according to the above-mentioned methods are set forth in the table below. In addition, the percentage of sebum reduction was calculated by dividing the point difference ($\Delta P$) by the number of points for the control group ($P_k$) and multiplying by 100%, as follows:

TABLE $$\text{Sebum reduction} = \frac{\Delta P}{P_k} \times 100\%.$$

| Example | Concentration (%) | Evaluation Method 1 | 2 | 3 | Sebum Reduction (%) |
|---|---|---|---|---|---|
| 1 | 0.25 | ++ | ++ | ++ | 84 |
| 2 | 0.1 | ++ | ++ | ++ | — |
| 3 | 0.1 | ++ | ++ | ++ | 68 |
| 4 | 0.1 | ++ | ++ | ++ | 66 |
| 5 | 0.1 | ++ | ++ | ++ | 65 |
| 6 | 0.5 | ++ | ++ | ++ | 42 |
| 8 | 0.5 | ++ | ++ | ++ | 69 |
| 9 | 0.1 | ++ | ++ | ++ | 84 |
| 10 | 0.1 | ++ | ++ | ++ | 27 |

Examples of topical cosmetic preparations according to the invention for the treatment of strongly oily hair and seborrhea are as follows:

Example 12

| Shampoo for Oily Hair | |
|---|---|
| Component | Parts by Weight |
| $C_{12}$–$C_{14}$—Fatty alcohol +2 EO sodium sulfate with 28% by weight of wash active substance (TEXAPON ® N, available from Henkel KGaA) | 42.5 |
| Ethanol amide of coconut fatty acid | 3.0 |
| Sodium chloride | 2.0 |
| Sodium sulfate | 2.0 |
| Compound of Example 1 | 0.1 |

-continued

| Shampoo for Oily Hair | |
| --- | --- |
| Component | Parts by Weight |
| d,l-α-Tocopherol | 0.1 |
| Perfume Oil | 0.1 |
| Water | 50.2 |
| | 100.0 |

Example 13

| Skin Cream | |
| --- | --- |
| Component | Parts by Weight |
| Self-emulsifying mixture of mono-diglycerides of higher saturated fatty acids with potassium stearate (CUTINA ® KD 16, available from Henkel KGaA) | 16.0 |
| Cetylstearyl alcohol with about 12 mols of ethylene oxide (EMULGIN ® Bl, available from Henkel KGaA) | 1.0 |
| 2-Octyldodecanol | 6.0 |
| Isopropyl myristate | 4.0 |
| Glycerin | 6.0 |
| Farnesol | 0.1 |
| Compound of Example 5 | 0.1 |
| Water | 66.8 |
| | 100.0 |

Example 14

| Hair Conditioner | |
| --- | --- |
| Component | Parts by Weight |
| Glycerin-monostearate and distearate (TEGIN ® M, available from Atlas Chemie) | 0.7 |
| Cationic surfactant | 2.0 |
| Cholesterol | 0.2 |
| Soy lecithin | 0.3 |
| Emulsifer (EMULGARDE ® A, available from Henkel KGaA) | 8.0 |
| Compound of Example 9 | 0.1 |
| BHT | 0.2 |
| Perfume oil | 0.3 |
| Water, demineralized | 88.2 |
| | 100.0 |

The preceding specific embodiments are illustrated of the practice of the invention. It is to be understood, however, that other expedients known to those skilled in the art or disclosed herein, may be employed without departing from the spirit of the invention or the scope of the appended claims.

We claim:

1. A method for treating oily hair or seborrhea which comprises administering to an individual in need of such treatment a sebosuppressively effective amount of one or more compounds of the formula $$Ar-CO-CH=CH-CO-X \quad (I)$$

wherein

Ar represents an optionally substituted aromatic or heteroaromatic group; and

X represents an alkoxy group having from 1 to 10 carbon atoms, an amino group optionally substituted by one or more aryl or alkyl groups having from 1 to 6 carbon atoms, or a nitrogen atom-containing heterocycle.

2. The method of claim 1, wherein Ar represents an optionally substituted phenyl, pyridyl, thienyl, furyl, or corresponding benzo analogue.

3. The method of claim 1, wherein Ar is substituted by one or more members selected from the group consisting of halogen, alkyl having from 1 to 6 carbon atoms, alkoxy having from 1 to 8 carbon atoms, hydroxyl, amino, alkylamino or dialkylamino wherein the alkyl moiety has from 1 to 6 carbon atoms, and acylamino having from 1 to 4 carbon atoms.

4. The method of claim 1, wherein:

Ar is a member selected from the group consisting of (1) hydrocarbon aryl, (2) hydrocarbon aryl substituted with substituents selected from the group consisting of halogen, alkyl having from 1 to 6 carbon atoms, alkoxy having from 1 to 8 carbon atoms, hydroxyl, amino, alkylamino having from 1 to 4 carbon atoms, dialkylamino having from 2 to 8 carbon atoms, and alkanoylamino having from 1 to 4 carbon atoms, (3) monocyclic heteroaryl containing heteroatoms selected from the group consisting of nitrogen, sulfur, and oxygen, (4) benzo analogs of said monocyclic heteroaryl, and (5) substituted monocyclic heteroaryl containing heteroatoms selected from the group consisting of nitrogen, sulfur, and oxygen, substituted with alkyl having from 1 to 6 carbon atoms, and X is a member selected from the group consisting of (6) alkoxy having from 1 to 10 carbon atoms, (7) phenylalkoxy having from 7 to 10 carbon atoms, (8) phenacyloxy, (9) amino having the formula

wherein $R_1$ is a member selected from the group consisting of alkyl having from 1 to 6 carbon atoms, hydroxyalkyl having from 1 to 6 carbon atoms, alkoxyalkyl having from 2 to 6 carbon atoms, and phenylalkyl where the alkyl moiety has from 1 to 6 carbon atoms and $R_2$ is a member selected from the group consisting of hydrogen and $R_1$, and $R_1$ and $R_2$ taken together are members selected from the group consisting of alkylene having 4 or 5 carbon atoms, alkylalkylene having from 5 to 10 carbon atoms, oxaalkylene having 4 or 5 carbon atoms, and alkyloxaalkylene having from 5 to 10 carbon atoms.

5. The method of claim 1, which contains from about 0.01 to 5 percent by weight of one or more compounds of Formula I, based upon the total weight of the cosmetic preparation.

6. The method of claim 1, which contains from about 0.05 to 10 percent by weight of one or more compounds of Formula I.

7. The method of claim 1, wherein the compounds are selected from the group consisting of 4-(3',4'-dimethoxy-phenyl)-4-oxo-but-2-enoic acid ethyl ester, 4-(4'-butoxy-phenyl)-4-oxo-but-2-enoic acid ethyl ester, 4-(4'-octyloxy-phenyl)-4-oxo-but-2-enoic acid ethyl ester, 4-(3',4'-dimethoxy-2'-hydroxy-phenyl)-4-oxo-but-2-enoic acid ethyl ester, and 4-phenyl-4-oxo-but-2-enoic acid diethylamide.

* * * * *

UNITED STATES PATENT AND TRADEMARK OFFICE
CERTIFICATE OF CORRECTION

PATENT NO. : 4,562,068

DATED : December 31, 1985

INVENTOR(S) : Hinrich Möller et al.

It is certified that error appears in the above-identified patent and that said Letters Patent is hereby corrected as shown below:

Column 6, line 31, "evulations" should read -- evaluations --.

Column 7, line 45, "illustrated" should read -- illustrative --.

Column 8, Claim 5, line 1, "contains" should read -- comprises administering --.

Column 8, Claim 6, line 1, "contains" should read -- comprises administering --.

Column 8, Claim 6, line 2, "10" should read -- 1.0 --.

Signed and Sealed this

Twenty-second Day of June, 1993

Attest:

MICHAEL K. KIRK

*Attesting Officer*   *Acting Commissioner of Patents and Trademarks*